United States Patent [19]
Shelton

[11] Patent Number: 5,836,989
[45] Date of Patent: Nov. 17, 1998

[54] METHOD AND APPARATUS FOR CONTROLLING AN IMPLANTED MEDICAL DEVICE IN A TIME-DEPENDENT MANNER

[75] Inventor: Michael B. Shelton, Minneapolis, Minn.

[73] Assignee: Medtronic, Inc., Minneapolis, Minn.

[21] Appl. No.: 777,840

[22] Filed: Dec. 26, 1996

[51] Int. Cl.$^6$ .............................. A61N 1/36; A61N 1/362
[52] U.S. Cl. .................................. 607/27; 607/9; 607/30
[58] Field of Search .................................. 607/9, 27, 30, 607/32, 55–57

[56] References Cited

U.S. PATENT DOCUMENTS

| | | | |
|---|---|---|---|
| 4,374,382 | 2/1983 | Markowitz | 340/870 |
| 4,428,378 | 1/1984 | Anderson et al. | 138/419 |
| 4,856,523 | 8/1989 | Sholder et al. | 128/419 |
| 4,944,298 | 7/1990 | Sholder | 128/419 |
| 4,958,632 | 9/1990 | Duggan | 128/419 |
| 5,052,388 | 10/1991 | Sivula et al. | 128/419 |
| 5,088,488 | 2/1992 | Markowitz et al. | 128/419 |
| 5,127,404 | 7/1992 | Wyborny et al. | 128/419 |
| 5,154,170 | 10/1992 | Bennett et al. | 128/419 |
| 5,226,413 | 7/1993 | Bennett et al. | 128/419 |
| 5,345,362 | 9/1994 | Winkler | 361/681 |
| 5,350,407 | 9/1994 | McClure et al. | 607/16 |
| 5,350,411 | 9/1994 | Ryan et al. | 607/32 |
| 5,360,437 | 11/1994 | Thompson | 607/30 |
| 5,372,607 | 12/1994 | Stone et al. | 607/30 |
| 5,421,830 | 6/1995 | Epstein et al. | 607/30 |
| 5,456,691 | 10/1995 | Snell | 607/30 |
| 5,456,692 | 10/1995 | Smith, Jr. et al. | 607/31 |
| 5,476,485 | 12/1995 | Weinberg et al. | 607/28 |
| 5,487,755 | 1/1996 | Snell et al. | 607/27 |
| 5,507,786 | 4/1996 | Morgan et al. | 607/27 |
| 5,549,649 | 8/1996 | Florio et al. | 607/15 |
| 5,653,735 | 8/1997 | Chen et al. | 607/9 |
| 5,722,999 | 2/1998 | Snell . | |
| 5,725,559 | 3/1998 | Alt et al. | 607/5 |

OTHER PUBLICATIONS

"Thera Product Information Manual," for Pacemark Models 89641, 89651, 89661 by Medtronic, Inc., undated.

*Primary Examiner*—William E. Kamm
*Assistant Examiner*—Carl H. Layno
*Attorney, Agent, or Firm*—Thomas F. Woods; Harold R. Patton

[57] ABSTRACT

An implantable medical device and corresponding system and method are disclosed having programmable operating functions for monitoring a patient condition or delivering a therapy. The device has a primary operating function and a trial operating function. Those functions are enabled or disabled in a time dependent manner to permit their comparison and evaluation in a patient. The device may include a telemetry transceiver for receiving external programmable sequences of operating instructions and for transmitting data externally to a programmer. The device may further include a memory for storing the sequence of operating instructions and for storing data related to the delivery of the therapy or the monitoring function.

17 Claims, 4 Drawing Sheets

METHOD AND APPARATUS FOR CONTROLLING AN IMPLANTED MEDICAL DEVICE IN A TIME-DEPENDENT MANNER

FIELD OF THE INVENTION

This invention relates to implantable medical devices having programmable operating functions for monitoring a patient condition or delivering a therapy, and more particularly to a system and method for controlling, in a time-dependent manner, an implantable medical device operating in a primary operating mode or in a trial operating mode.

BACKGROUND OF THE INVENTION

A wide variety of implantable medical devices have been developed over the years, including human tissue electrical stimulators, monitors, cochlear implants, drug dispensers and the like. Known dual chamber, implantable cardiac stimulators, pacemakers, pacemaker-cardioverter-defibrillators (PCDs), implantable cardioverter-defibrillators (ICDs), and implantable cardiac monitors sense and discriminate a trial and ventricular heart activity, store data and control other operations. For example, a trial and ventricular pacing may be synchronized with a sensed underlying heart rhythm, or a trial and ventricular tachyarrhythmias may be discriminated from one another.

Implantable cardiac stimulators have progressively become more sophisticated and capable of performing a wide variety of functions in response to a variety of sensor input signals. The signal processing and operating control systems of such cardiac stimulators and monitors typically comprise a memory for retaining operating modes and parameter values that are remotely programmable employing an external programmer. An early microcomputer based operating system for such an implantable cardiac stimulator is described in U.S. Pat. No. 4,958,632, hereby incorporated by reference herein in its entirety.

At the present time, typically at least several operating modes and parameters are remotely programmable to permit the cardiac stimulator to diagnose one or more cardiac arrhythmias and deliver an appropriate therapy. Typically, the implanted stimulator has an operating system and algorithm that provide a primary operating mode and one or more optional programmable operating modes that may be selected and programmed by the physician to replace the primary operating mode. Within a given operating mode, a set of default operating parameter values are defined therein. Programmable parameter values are also provided that may be selected and programmed as the current operating parameter value.

Typically, operating modes and parameter values are stored in memory within the implanted device and called up by the microcomputer or used to control digital logic during an operating cycle corresponding to a pacing escape interval. In cardiac pacemakers, the pacing rate in one or both heart chambers is typically controlled by algorithms. Those algorithms process signals corresponding to the underlying cardiac rhythm and physiologic parameters such as patient activity level to arrive at a suitable pacing escape interval and corresponding pacing rate. The pacemaker operating modes and the algorithm for establishing the appropriate pacing rate are programmable in memory internal to the device by accessing the implanted pacemaker's telemetry transceiver with an external programmer during a downlink telemetry transmission.

Similarly, in PCD systems the diagnosis of a tachyarrhythmia requiring delivery of a treatment therapy and the selection of the appropriate therapy corresponding to such a tachyarrhythmia are controlled by operating modes and algorithm parameters that may be programmed in device memory using an external programmer.

Cardiac stimulators typically process patient electrograms and acquire or measure physiological data for diagnosis. Such data is usually stored, especially if they relate to intrinsic heart rate or arrhythmic episodes. Stored data may be subsequently uplinked by telemetric means by interrogating device memory using an external programmer. Such telemetered data are then analyzed, and may be employed to establish or refine the operating modes and parameters of the device operating algorithms. For example, the implantable device may be re-programmed to operate in a new mode or a new parameter value may be downloaded into memory.

A wide variety of programming and interrogation techniques have been devised for implantable medical devices. Examples of current medical device programmers include the Medtronic® Model 9760 pacemaker programmer and the Model 9790 universal programmer for bradycardia pacemakers and tachyarrhythmia devices. Those devices are described in U.S. Pat. Nos. 5,372,607, 5,345,362, and 5,350,411, and in U.S. patent application Ser. No. 08/228,237 filed Apr. 15, 1994. The foregoing patents are hereby incorporated herein by reference in their respective entireties.

The "THERA® s Product Information Manual" published by MEDTRONIC®, Inc. for Pacemaker Models 8964 i, 8965 i and 8966 i describes the operation of a typical modern pacemaker, and is hereby incorporated herein in its entirety.

A physician typically diagnoses a patient's medical condition to determine whether or not a bradycardia or tachycardia condition exists. An appropriate cardiac pacing system is then selected that is capable of automatically detecting and providing pacing pulses in response to episodes of the determined arrhythmia. If a particular arrhythmia is not readily observable, the patient may be fitted with an external cardiac monitor to record arrhythmic episode data for later analysis. The appropriate cardiac pacing system is selected from among many such systems offered by various manufacturers. Those systems vary generally in respect of the features they provide and the price for which they may be purchased.

After the selected device is implanted, the patient is periodically examined to ensure the system is responding appropriately to the arrhythmia. Operating modes and parameter values may be reprogrammed by the physician to optimize performance of the system. Data stored in the device memory may be telemetered to an external device for subsequent analysis. At times a physician may have difficulty determining which operating mode or parameter values will yield optimum results for a given patient. Uncertainty in selecting modes or values is often heightened by the limited amount of time physicians have to spend with individual patients. Sometimes it is impossible for a physician to evaluate with any degree of confidence how well or appropriately a cardiac stimulator might or will operate in different operating modes or with different parameter values loaded in device memory within the limited amount of time he has to observe a patient.

An alternative process of sequentially re-programming operating modes or parameter values during serial patient visits, enabling data acquisition in memory between patient visits, telemetering data from the device, and evaluating those data is burdensome and time consuming.

Because a wide spectrum of patient conditions exists, and because advances in patient diagnosis and treatment occur continuously, manufacturers develop new pacing systems on an on-going basis. Each new system must satisfy rigorous regulatory examination and approval. One means of ameliorating the burden of developing and obtaining regulatory approval for each new system is to replace or customize the original operating system software by downloading a substitute operating system.

U.S. Pat. No. 5,456,691, hereby incorporated by reference herein in its entirety, describes a control program for operating the implanted medical device in accordance with a program module selected by the physician. After the program module is selected, the control program is re-compiled and reprogrammed in the memory of the implanted device. The device operates until the physician determines an additional or alternative program module should be selected. Other newer or updated program modules may be developed and offered to the physician for incorporation into the control program at a later date.

U.S. Pat. No. 5,456,692 describes a control program that may be replaced by a new control program when it becomes available. An underlying safety mode of the implanted device becomes operational when the new control program is downloaded. A basic pacing mode is provided by a back-up control program or device hardware during the downloading time period. Alternatively, the control program may be transferred to a temporary memory location and used to operate the device while the substitute control program is being downloaded. Device operation may be controlled by the replacement control program after it has been confirmed that the replacement program has been downloaded successfully and has been installed correctly in memory.

While the foregoing approaches are meritorious, they do not relieve the regulatory approval burden attending the use of each new control program or new control module. It may still be necessary to submit clinical evidence of safety and efficacy obtained through expensive, lengthy clinical evaluations. Moreover, if a patient can receive therapeutic benefit by having his existing device explanted and a new device implanted, or by having new software downloaded into his existing implanted device, either approach requires significant time and expense.

For example, downloading new software in serial fashion or implanting a new device requires physician time, hospital or clinical expenses, medical device and operation costs, patient time, and research and development by the medical device manufacturer. In other words, payment of some sort is required. Additionally, even if new software is downloaded or an implanted device is replaced, there is no guarantee that the new software or the new device will provide an optimum or even better therapeutic benefit than that provided by the previously employed software or device. This is because in respect of the patient himself the therapeutic benefit of the new program or device remains unknown until after it has been rendered operational within him.

Implantable cardiac stimulators are well known in the art, some examples of which may be found in the issued U.S. Patents listed in Table 1 below.

TABLE 1

| Patent Number | Prior Art Patents Title |
|---|---|
| 4,856,523 | Rate-Respiratory Pacemaker with Automatic Switching and/or Variable Hysteresis Rate |
| 4,944,298 | Atrial rate Based Programmable Pacemaker with Automatic Mode Switching Means |

TABLE 1-continued

| Patent Number | Prior Art Patents Title |
|---|---|
| 5,088,488 | Method and Apparatus for Implementing Histogram Storage and Trend Analysis in a Medical Stimulator |
| 5,226,413 | Rate Responsive Pacemaker and Method for Automatically Initializing the Same |
| 5,350,407 | Implantable Stimulator Having Quiescent and Active Modes of Operation |
| 5,360,437 | Implantable Medical Device with Flexible Hardware Platform |
| 5,456,691 | Programming System Having Multiple Program Modules |
| 5,456,692 | System and Method for Noninvasively Altering the Function of an Implanted Pacemaker |
| 5,476,485 | Automatic Implantable Pulse Generator |
| 5,487,755 | Methods for Displaying a Sequential Series of Pacing Events |
| 5,549,649 | Programmable Pacemaker Including an Atrial Rate Filter for Deriving a Filtered Atrial Rate Used for Switching Modes |

All patents listed in Table 1 hereinabove are hereby incorporated by reference herein in their respective entireties. As those of ordinary skill in the art will appreciate readily upon reading the Summary of the Invention, Detailed Description of the Preferred Embodiments and Claims set forth below, many of the devices and methods disclosed in the patents of Table 1 may be modified advantageously by using the teachings of the present invention.

SUMMARY OF THE INVENTION

The term "object" as employed herein means the provision of a solution to a problem existing in the prior art. The medical device and corresponding system and method of the present invention have one or more of the following objects:

(a) paying only for those therapies delivered by an implantable medical device that provide a benefit to the patient;

(b) reducing medical costs generally;

(c) efficiently and timely determining optimum therapies for implanted medical devices (d) permitting physicians to quickly and more efficiently acquire and evaluate clinical data acquired using implanted medical devices;

(f) reducing research and development costs for medial device manufacturers, and (g) reducing regulatory approval burdens for medical device manufacturers.

The implantable medical device and corresponding system and method of the present invention have at least one of the following features:

(a) means for acquiring and storing in data memory trial operating mode or function data and reference operating mode or function data;

(b) means for alternately or successively acquiring and storing in data memory trial operating mode or function data and reference operating mode or function data;

(c) means for acquiring and storing in data memory trial operating mode or function data that may be selectively disabled by a physician;

(d) means for acquiring and storing in data memory trial operating mode or function data that are automatically disabled after a predetermined period of time;

(e) means for enabling or disabling one or more trial operating modes or functions;

(f) means for enabling or disabling one or more reference operating modes or functions;

(g) means for enabling or disabling one or more trial parameter values;

(h) means for enabling or disabling one or more reference parameter values;

(i) telemetric means for uploading or downloading trial or reference data;

(j) telemetric means for uploading or downloading upgraded or new control programs or program modules for the implanted device;

(k) means for comparing and analyzing reference and trial data, and (l) external means for programming the implanted device.

The present invention provides at least one of the following advantages:

(a) patients, health care insurance companies, and health care maintenance organizations (HMOs) not having to pay for medical devices, or therapies implemented by such devices, that do not provide a benefit to the patient;

(b) determining the optimum therapy a patient should receive before any payment is made;

(c) reducing health care costs;

(d) permitting physicians to acquire potentially valuable and useful clinical data at no additional cost to the patient, a health care insurance company, or HMO;

(e) providing maximum therapeutic flexibility to the patient and physician;

(f) providing patients with only those therapies they require;

(g) not providing patients with those therapies they do not require; and (h) effectively delivering the most effective medical therapies to patients at the lowest cost.

The foregoing and other objects, features and advantages of the present invention will be more readily understood by referring to the following detailed description of the preferred embodiments, and appended claims and figures, wherein like numerals refer to like structures and features throughout.

DETAILED DESCRIPTION OF THE PREFERRED EMBODIMENTS

The term "trial" as used herein refers to operating modes in an implantable medical device that are employed for evaluative, experimental, short-term or clinical purposes.

The terms "primary" or "reference" as used herein refer to operating modes in an implantable medical device that are not employed for evaluative, experimental, short-term or clinical purposes.

The present invention provides a time dependent, clinical evaluation regimen for successively enabling, during a trial time period, and disabling, during a reference time period, a trial mode or trial function in the device, system or corresponding method of the present invention. That is, during any one period of time a trial operating mode or function, one or more trial parameter values, a reference mode or function, or one or more reference parameter values may be enabled or disabled in an implanted medical device. Those modes, functions or parameter values may optionally be individually, serially, successively or alternately enabled or disabled. According to the device and corresponding system and method of the present invention, both trial data and reference data are acquired and stored for later retrieval using the same patient as the test subject and control subject. The present invention may also provide at least one new trial operating function or mode in a previously implanted medical device, where the trial mode or trial function operates on a temporary or permanent prescription basis therein.

More than one trial mode or trial function may be provided. In a previously implanted medical device, trial data and reference data may be individually, serially, alternately, or successively acquired and stored in data memory. A physician may later upload the stored trial and reference data from the device, and comparatively analyze those data to determine whether or not the patient benefits from one of the trial operating modes or functions.

The present invention may further provide a time dependent, clinical evaluation regimen for successively enabling, during a trial time period, and disabling, during a reference time period, a trial mode or trial function in the device, system and corresponding method of the present invention. That is, during a trial period of time, a trial operating mode or function, or one or more trial parameter values, may operate while enabled. Similarly, during a reference time period, a reference mode or function, or one or more reference parameter values, may operate while enabled.

Trial and reference modes may be individually, serially, successively, or alternately enabled and disabled according to the capabilities of the particular device at hand and the discretion of the attending physician. Trial and reference modes of the present invention most preferably do not operate at the same time. Instead, each mode most preferably operates only when the other mode is not operating. Each such mode may be disabled by terminating its operation. While operating in either trial or reference mode, sensed data may be acquired by the device for storage in device memory.

In another embodiment of the present invention, a primary operating mode is enabled during a primary operating time period. The primary operating mode may have a set of primary parameter values associated therewith. A trial operating mode is enabled during a trial operating time period, where the trial operating time period does not coincide with the primary operating time period. The trial operating mode may also have a set of trial operating parameter values associated therewith. After trial and reference data have been acquired and stored in memory in the device of the present invention, the reference and trial data may be compared and analyzed to arrive at an optimum operating mode or function, or optimum parameter value.

In another embodiment of the present invention, a medical device is implanted in a patient. The device has an operating memory therein for storing a first programmable sequence of operating instructions that govern a primary operating mode or function of the device. The operating memory also accepts and stores therein a second programmable sequence of operating instructions that govern a trial operating mode or function of the device. Optionally, both the first sequence and second sequence may include instructions for storing and executing reference or trial parameter values. The execution of those values then enables or disables a reference or trial operating mode or function.

In a preferred embodiment of the device and corresponding system and method of present invention, there exist one or more means for: (a) executing a sequence of operating instructions that enable a primary operating function or mode during a reference time period; (b) acquiring and storing reference data when the primary operating mode or function is enabled during the reference time period; (c) executing a sequence of operating instructions that enable a trial operating mode during a trial time period; and (d) acquiring and storing trial data when the trial operating mode or function is enabled during the trial time period.

The implanted medical device or system of the present invention preferably includes a data memory for storing acquired reference and trial data. A telemetry system is preferably included in the device or system that telemeters data stored in data memory in the device to an external programmer when a preprogrammed (or programmed) interrogation command is received. The device and system of the present invention may also include external means for programming the device. Such external programming means may interrogate the memory of the implanted device and retrieve reference and trial data stored therein. Most preferably, those data may then be evaluated, compared and analyzed in the programming means by a user to evaluate the efficacy or benefit provided by the trial operating mode or function, or executed trial parameter value.

In one embodiment of the present invention, an implantable medical device provides a therapy or monitoring function under the control of a programmable sequence of operating instructions that govern the operating function of the device. A telemetry transceiver disposed in the device is capable of receiving externally provided programmed sequences of operating instructions. The implantable device is most preferably capable of transmitting data (such as trial and reference data stored in the data memory of the device) to an external device. The storage memory on the device preferably stores a sequence of operating instructions or data related to the delivery of the therapy. The device may also have a monitoring function that is employed in conjunction with an external programmer, where a trial operating function is programmable the device for a trial time period.

In the present invention, the method may comprise the steps of, and the implantable medical device may comprise means for using the programmer in conjunction with an implantable device for: (i) programming a primary operating function in the device to define a primary operating mode and operating parameters; (ii) programming a trial operating function in the device to define a trial operating mode or parameter value for delivery of a trial therapy or a monitoring function; (iii) programming the device to acquire and store reference data and trial data; and (iv) programming the device with a trial commence time, a trial end time, or a trial time period during which the trial operating function is enabled.

In the present invention, the method may further comprise the steps of, and the implantable medical device may further comprise means for: (i) timing out a current real time; (ii) comparing the current real time to the trial commence time and trial end time; (ii) between the commence time and the end time, operating the medical device in accordance with the trial operating function and acquiring trial data; and (iii) at other times, operating the medical device in accordance with the primary operating function and acquiring reference data.

In the present invention, the method may yet further comprise the steps of, and the implantable medical device may yet further comprise means for using an external programmer to interrogate device memory and retrieve reference and trial data stored therein for use in evaluating the efficacy of a trial operating function.

The present invention may further provide a device, system or corresponding method, wherein a new trial operating mode or function is implemented in an implanted medical device operating in a patient, a trial mode is activated and evaluated in accordance with the methods described above, and the trial mode is later prescribed on a permanent basis or not prescribed following a trial period during which trial and reference data are acquired and stored by the device. Most preferably, permanent prescription of the new trial operating function is made only after the evaluation establishes that the new function provides therapeutic benefits to the patient. Upgraded control programs or program modules may be downloaded by physicians for use and evaluation during trial time periods in patients. A monetary charge or fee may attend the trial or permanent prescription.

In a pre-market release device, clinical evaluation of a trial function or mode may be implemented by a sequence of operating instructions constituting the control program or a program module. In the present invention, the method may comprise the steps of, and the device may comprise means for programming a time dependent, clinical evaluation regimen for successively enabling, during a clinical trial period, and disabling, during a rest trial period, a trial device function. That is, a particular therapy or monitoring diagnostic function may be enabled or disabled in an implanted medical device so that both test data and control data may be acquired using the same patient as the test subject and control subject.

The clinical evaluation regimen providing the successive clinical trial periods and reference periods may also be advantageously used at market release to determine the efficacy of a trial device function selected from the available operating modes and parameter values in treating or monitoring a given patient.

In all of these contexts, advantage may be taken of the ability of the implanted device to gather and store data related to the trial mode or function for use in evaluating its efficacy.

The present invention may be practiced using the basic hardware and software of existing microprocessor-controlled, multi-programmable, implantable 10 cardiac stimulators, monitors and other medical devices. Naturally, it is preferable when practicing the present invention that such devices have uplink and downlink telemetry capabilities and an external, microprocessor-based programmer.

Figure 1:
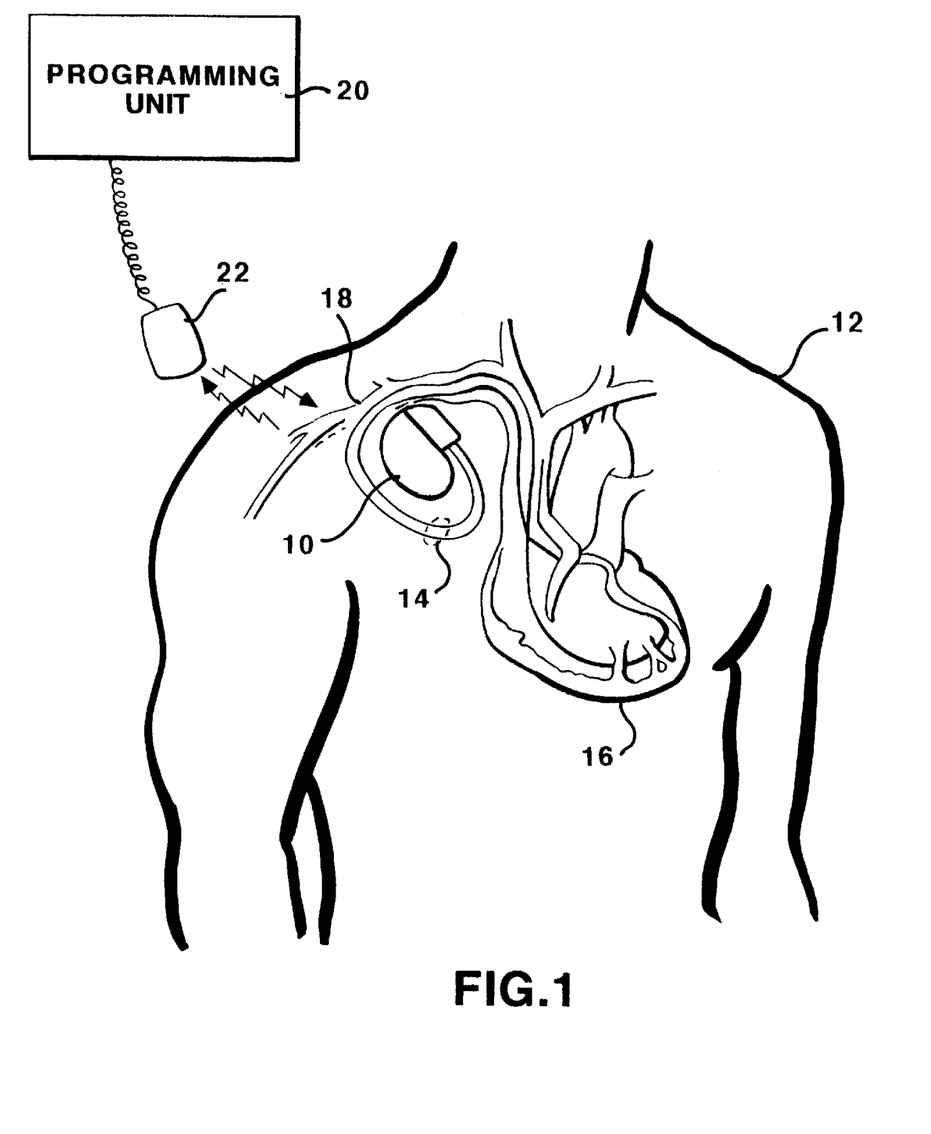
FIG. 1 shows a simplified view of an implanted medical device in a patient and an external programmer for providing uplink and downlink telemetry with the implanted device in which the present invention may be implemented.
Figure 2:
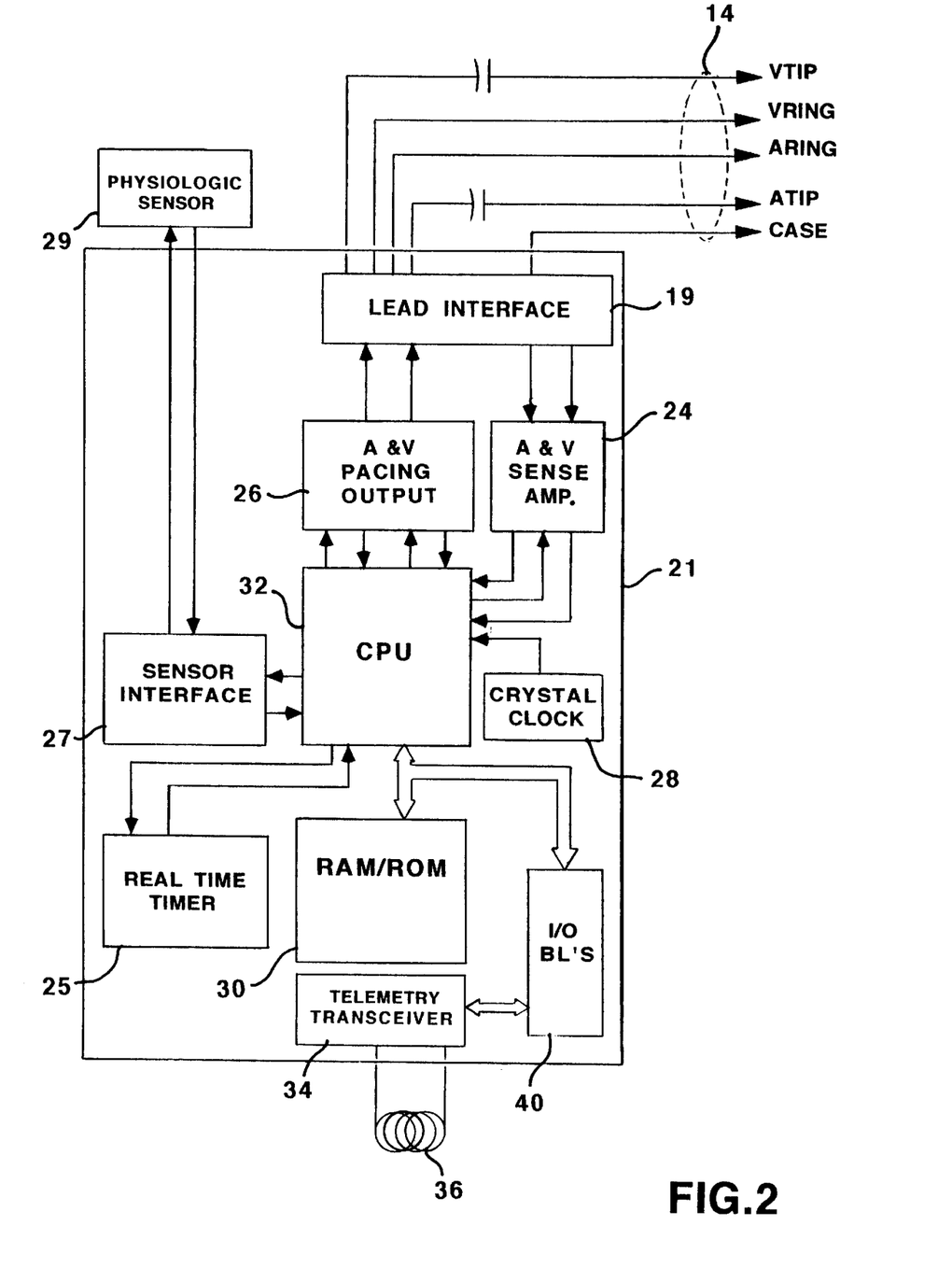
FIG. 2 shows a simplified block diagram of the major components of the implanted medical device of FIG. 1.
Figure 3:
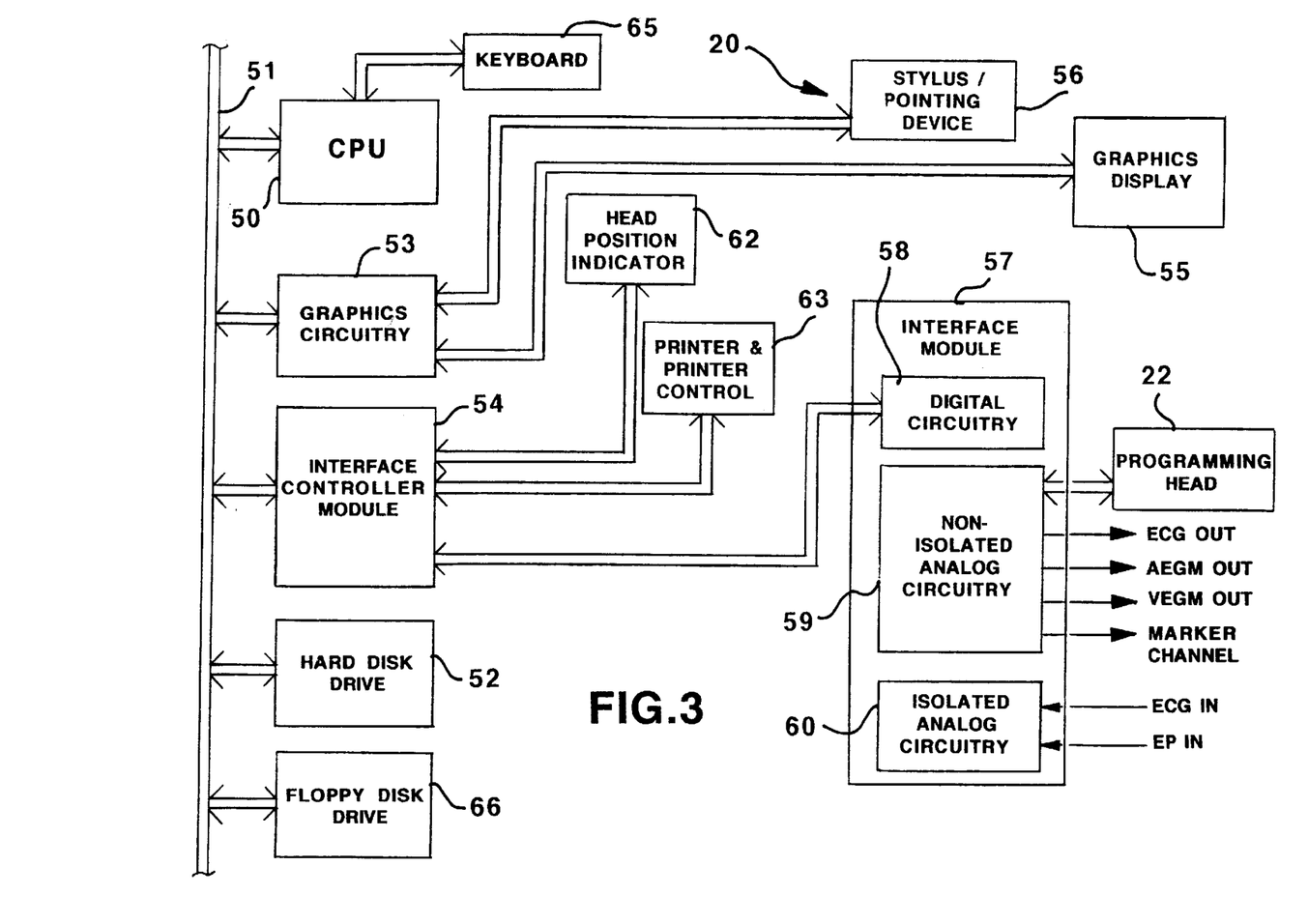
FIG. 3 shows a simplified block diagram of the major components of the external programmer of FIG. 1.

The system of the present invention shown in FIGS. 1–3 includes a dual chamber, rate responsive implantable pulse generator (IPG) 10 implanted in patient 12 and capable of operating in a number of primary operating modes, including the DDDR mode. A control program is downloaded in IPG 10 using an external programmer 20 and telemetry.

In accordance with conventional practice in the art, pacemaker IPG 10 is housed within a hermetically sealed, biologically inert outer canister, which may itself be conductive so as to serve an indifferent electrode in the pacemaker's pacing or sensing circuits. One or more pacemaker leads, collectively identified with reference numeral 14 in FIG. 1, are electrically coupled to IPG 10 in a conventional manner and extend into the patient's heart 16 via a vein 18. Disposed generally near the distal end of leads 14 are one or more exposed conductive electrodes for receiving electric cardiac signals or for delivering electrical pacing pulses to heart 16. As will be appreciated by those of ordinary skill in the art, leads 14 may be implanted with their distal ends positioned in either the atrium or ventricle heart 16.

External programmer 20 is provided for non-invasive communication with implanted pacemaker IPG 10 via uplink and downlink telemetry. Associated with programmer 20 is programming head 22 for facilitating telemetric communication between implanted IPG 10 and programmer 20. Programming head 22 is positioned on the patient's body over the implant site of the IPG 10, such that one or more antennae within head 22 may send pulse modulated RF signals to, and receive pulse modulated RF signals from, an antenna disposed within the hermetic enclosure of the implanted IPG 10.

FIG. 2 depicts a block diagram of the major components of a DDDR IPG 10, and includes primary control circuit 21 for controlling the device's pacing, sensing, programming and data telemetry functions. Control circuit 21 in FIG. 2 includes sense amplifier circuit 24, stimulating pulse output circuit 26, a crystal oscillator clock 28, a random-access memory and read-only memory (RAM/ROM) unit 30, controller/timer central processing unit (CPU) 32, internal telemetry transceiver 34, and I/O bus 40, all of which components are well-known in the art. Lead interface 19 is provided for coupling the atrial and ventricular pacing output circuits 26 and sense amplifier circuits 24 to the atrial and ventricular leads 14.

One or more physiologic sensors 29, such as a lead borne blood pressure sensor, a case mounted activity sensor, or an impedance plethysmograph system, are coupled through sensor interface 27 to the controller/timer CPU 32 for setting a pacing escape interval dependent on a rate control algorithm. See, for example, U.S. Pat. No. 5,154,170, hereby incorporated by reference herein in its entirety. The rate control algorithm is responsive to the sensor output signal and one or more weighting factors having a programmable parameter value. The specific connections between the circuit blocks and the lead interface 19 and I/O interface 40 are shown in a simplified representation in FIG. 2. Control circuit 21 may be of conventional design.

Various components of IPG 10 depicted in FIG. 2 are powered by means of a battery (not shown) which is contained within the hermetic enclosure of IPG 10. For the sake of clarity in the figures, the battery and the connections between it and the other components of IPG 10 are not shown.

Control of timing and other functions within the control circuit 21 is provided by CPU 32, which may include an off-the-shelf or custom design microprocessor or microcontroller associated with digital logic and timers. Although specific connections between CPU 32 and the other components of control circuit 21 are simplified in FIG. 2, it will be apparent to those of ordinary skill in the art that CPU 32 functions to control the timed operation of stimulating pulse output circuit 26 and sense amplifier circuit 24 under control of operating algorithm firmware stored in RAM/ROM unit 30 that controls the operation in conjunction with the primary operating modes and parameter values that are programmable and stored in RAM/ROM unit 30.

Controller/timer CPU 32 defines the basic pacing or escape interval. Pacing and escape intervals generally take one of two forms. In the first form, A—A escape intervals are initiated upon sensing of an atrial event (A-event) or a pacing event (A-pace), or are initiated upon the triggering of an atrial pacing event (A-pace). In the second form, V—V escape intervals are initiated upon the sensing of a ventricular event (V-event) or a ventricular pacing event (V-pace), or are initiated upon the triggering of a ventricular pacing event (V-pace).

Controller/timer CPU 32 similarly defines separate A-V delay intervals SAV and PAV that commence following a sensed A-event and a delivered A-pace, respectively.

Controller/timer CPU 32 also defines time intervals for controlling operation of the atrial and ventricular sense amplifiers in sense amplifier circuit 24. Typically, controller/timer CPU 32 defines an atrial blanking interval following delivery of an A-pace or a V-pace pulse, during which time atrial sensing is disabled. CPU 32 typically defines ventricular blanking intervals following delivery of a V-pace pulse, during which time ventricular sensing is disabled. Digital controller/timer CPU 32 also defines an atrial refractory period (ARP) during which time atrial sensing is disabled or the A-event is ignored for the purpose of resetting the escape interval. The ARP extends from the beginning of the SAV or PAV interval following either an A-event or an A-pace pulse and until a predetermined time following sensing of a ventricular depolarization or triggering the delivery of a V-pace pulse.

Controller/timer CPU 32 similarly defines a ventricular refractory period (VRP), which is typically shorter than the portion of the ARP following ventricular sensing or pacing, following either a V-event or V-pace pulse. In the case of an ectopic V-event, both a VRP and a post-ventricular atrial refractory period (PVARP) defined by the controller/timer CPU 32 separately from the ARP may be generated. The durations of the ARP, PVARP and VRP may also be programmed in the RAM in RAM/ROM unit 30.

Controller/timer CPU 32 also controls sensitivity settings of the sense amplifiers 24 in accordance with programmable sensitivity parameter values stored in RAM in RAM/ROM unit 30. Typically, a range of sensitivity parameter values are provided for the physician to select from to ensure that the sense amplifiers are not oversensing noise or other signals or not undersensing true atrial and ventricular events (P-waves and R-waves).

Controller/timer CPU 32 also controls the A-pace and V-pace pulse energies in accordance with programmed pulse amplitude and pulse width parameter values stored in RAM in RAM/ROM unit 30. Typically, a range of pulse widths and amplitude parameter values are provided for the physician to select from to ensure that the pacing pulse energy is sufficiently high to capture the atria or ventricles, but not so high as to unduly waste battery energy.

Telemetry transceiver 34 is coupled to the telemetry antenna 36 and is operated under the control of CPU 32 in a downlink telemetry mode for receiving, decoding and storing programmable commands and data in RAM/ROM unit 30. Transceiver 34 also operates in an uplink telemetry mode for encoding and transmitting out stored data and certain digitized real time data. The telemetry system described in the above-referenced '411 patent and in U.S.

Pat. No. 5,127,404, hereby incorporated herein by reference in its entirety, set forth pulse modulation encoding and decoding regimens for the data bits encoded within the RF telemetry signals.

Sensor interface circuit 27 and associated physiologic sensor 29 may correspond to the circuitry disclosed in U.S. Pat. Nos. 5,052,388 and 4,428,378, hereby incorporated herein by reference in their respective entireties. Similarly, the present invention may be practiced in conjunction with other sensors such as respiration sensors, blood oxygen sensors, pressure sensors, pH sensors or temperature sensors. The present invention may also be practiced in non-rate responsive pacemakers and other implanted, programmable medical devices capable of storing reference and trial data as described herein.

If IPG 10 is programmed to a rate responsive mode, the patient's activity level is monitored periodically and the escape interval is adjusted proportionally. A timed interrupt may be provided to allow CPU 32 to analyze the rate determining output signal of the sensor interface circuit 27 and update the escape interval (A—A or V—V). CPU 32 may also define variable A-V intervals and variable ARPs and VRPs which vary with the escape interval established in response to the measured physiologic parameter.

CPU 32 also controls the sensitivity or responsiveness of the physiologic sensors 29 and the processing of the output signals of the physiologic sensors 29 in the sensor interface circuit 27 in accordance with programmed rate determining parameter values stored in RAM in RAM/ROM unit 30. Typically, a range of rate determining parameter values and sensor sensitivity adjustment parameter values are provided for the physician to select from to ensure that the resulting rate determining output signal results in an optimal escape interval for establishing a level of cardiac output appropriate to the activity level of the patient. See, for example, the above-referenced '170 patent.

In the present invention, additional real time timer 25 may be provided in control circuit 21. In practice, timer 25 may be a timer function of CPU 32. Timer 25 may be employed in conjunction with programmed commence and end times to alternatively operate control circuit 21 in accordance with the primary operating function or a trial operating function so that reference and trial data may be acquired for use by the physician in evaluating a trial operating function.

The physician may select commence and end times to establish periodic trial time periods that recur on a daily basis, more than once a day, or on a less frequent basis. The physician programs those times into RAM in RAM/ROM unit 30. The primary operating function comprises the programmed, permanent operating mode and parameter values. The trial operating function may comprise an alternative mode, one or more alternative parameter values, or a combination of both.

A generalized block diagram of programmer 20, such as the Medtronic® Model 9760 or 9790 programmer described in detail in the above-referenced '362 patent, is shown in FIG. 3. Programmer 20 may be a personal computer or other microprocessor-based device having a central processing unit 50 such as an INTEL® 80386 or 80486 or PENTIUM microprocessor or the like. A system bus 51 interconnects CPU 50 with hard disk drive 52 for storing operational programs and data, graphics circuit 53, and interface controller module 54. Floppy disk drive 66 (or CD ROM drive 70 shown in FIG. 4) is also coupled to bus 51 and is accessible via a disk insertion slot (shown as slot 68 in FIG. 4) within the housing of programmer 20. Programmer 20 further comprises an interface module 57 which includes digital circuit 58, non-isolated analog circuit 59 and isolated analog circuit 60. Digital circuit 58 enables interface module 57 to communicate with interface controller module 54.

For the physician or other care giver to communicate with programmer 20, keyboard 65 coupled to CPU 50 is optionally provided. However, the primary mode of communication for a user is preferably through graphics display screen 55 of the "touch sensitive" type controlled by graphics circuit 53. A user of programmer 20 may interact therewith through the use of stylus 56, also coupled to graphics circuit 53, which points to various locations on screen 55, and displays menu choices for selection by the user. An alphanumeric keyboard may also be employed by the user for entering text, numbers or other symbols as shown in the above-referenced '362 patent. Various other touch-screen assemblies are known and may be used in conjunction with the present invention. Graphics display screen 55 displays patient related data, menu choices and data entry fields.

Graphics display 55 may also display a variety of data respecting data is telemetry. Programmer 20 may also be provided with strip chart printer 63 coupled to interface controller module 54. A hard copy of a patient's ECG, electrogram (EGM), marker channel or of graphics displayed on display 55 may be printed out.

It is often desirable to provide a means for programmer 20 to adapt its mode of operation depending upon the type or generation of implanted medical device to be programmed. Accordingly, it may be desirable to have an expansion cartridge containing EPROMs or the like for storing software programs to control programmer 20 to operate in a manner of the present invention that corresponds to a given type or generation of implantable medical device. In addition, it may be desirable to provide an expansion cartridge, floppy disk drive 66, CD ROM drive 68 (shown in FIG. 4) for introducing a new operating algorithm. The new operating algorithm may then replace the primary operating algorithm of the implanted device.

Non-isolated analog circuit 59 of interface module 57 is coupled to a programming head 22 which is used to establish the uplink and downlink telemetry links between IPG 10 and programmer 20. Atrial and ventricular sense amp circuits 24 of IPG 10 may also be provided with EGM amplifiers which produce atrial and ventricular EGM signals. These A-EGM and V-EGM signals may be digitized and uplink telemetered to programmer 20 on receipt of a suitable interrogation command. The uplink telemetered EGM signals are received in programming head 22 and provided to non-isolated analog circuit 59. Non-isolated analog circuit 59, in turn, converts the digitized EGM signals to analog EGM signals (as with a digital-to-analog converter, for example) and presents those signals on output lines designated in FIG. 3 as A-EGM OUT and V-EGM OUT. Those output lines may then be applied to strip-chart recorder 63 to provide a hard-copy printout of the A-EGM or V-EGM signals for viewing by the physician. As those signals are derived from intracardiac electrodes, they often provide information that may not appear in conventional surface ECG signals derived from skin electrodes.

IPG 10 may also be capable of generating so-called marker codes indicative of the different cardiac events it detects. A pacemaker with marker-channel capability is described, for example, in U.S. Pat. No. 4,374,382 to Markowitz, which patent is hereby incorporated by reference herein in its entirety. The markers provided by pacemaker IPG 10 may be received by programming head 22 and presented on the MARKER CHANNEL output line from non-isolated analog circuit 59.

Isolated analog circuit 60 in interface module 57 receives external ECG and electrophysiologic (EP) stimulation pulse signals. Analog circuit 60 receives ECG signals from patient skin electrodes and processes those signals before providing them to the remainder of the programmer system. Circuit 60 may receive EP stimulation pulses from an external EP stimulator for non-invasive EP study purposes.

To ensure proper positioning of programming head 22 over antenna 36 of IPG 10, the physician is provided with feedback to indicate that programming head 22 is in satisfactory communication with and is receiving sufficiently strong RF signals from antenna 36 of IPG 10. This feedback may be provided, for example, by means of a head position indicator such as a light-emitting diode (LED) that illuminates when a stable telemetry channel exists.

In the present invention, IPG 10 is preferably supplied to a physician with a primary operating function for providing a basic DDD or DDDR pacing therapy. Such a therapy is typically defined by a predetermined array of programmable bradycardia or tachycardia pacing and monitoring modes. A number of programmed operating parameter value and mode options may be provided in such an array. Most preferably, IPG 10 is initially programmable a primary operating mode such as a dual chamber DDD or DDDR pacing mode, wherein pacing pulses are delivered to the right atrium and ventricle in A-V synchrony, and wherein sensed atrial and ventricular depolarizations inhibit delivery of pacing pulses.

IPG 10 may be capable of operating in either single chamber or dual chamber modes, and of operating in at least one of the VVI, AAI, DDI, DVI, DVIR and DDIR modes. Any one of these operating modes may be programmed as the primary operating mode of the primary operating function or as an operating is mode of a trial operating function. Apart from these operating modes, a variety of the other operating parameter values selected from a range of possible parameter values described above may be programmed as a primary parameter value in the primary operating function or as a trial parameter value in a trial operating function.

Ranges of operating modes and parameter values of the present invention may be provided in IPG 10 when the device is used for clinical evaluation purposes or when it is released to the market. The present invention is particularly useful for the clinical evaluation of a new operating function embodied in software capable of being loaded and programmed in the memory of IPG 10 before the device is approved by the FDA for general market release.

From time to time during the operating life of IPG 10 in a given patient, a new or revised operating mode or set of parameter values may be provided for evaluation on a trial basis, either in a clinical evaluation or in a market release context. Those modes or parameter values may constitute fairly simple changes to existing, available parameter values. Conversely, those modes or values may constitute complicated new arrhythmia detection algorithms for processing A-sense or V-sense events, or new rate determining algorithms for use in the sensor interface.

As described in the above-referenced '691 and '692 patents, where the primary operating algorithm is stored primarily in RAM or the like, an entirely new primary operating algorithm or control program, or a change in a component or program module thereof, may be devised and provided on a trial basis to the physician and patient. In accordance with the present invention, the efficacy of the new control program or program module may be evaluated in a given patient at no cost to the patient, physician, HMO or health insurance company, where the patient is employed as both the test and control subject. During an evaluation period defined by the programmed evaluation or trial time period, the physician may program selected combinations of pacing or monitoring modes, and may observe their efficacy in treating or diagnosing the patient.

Software defining the trial operating function may be distributed through magnetic diskettes, by modem, through the Internet, or by telemetric means. Whatever means of distribution are employed, appropriate safeguards should be used to ensure use of the software only by a qualified physician responsible for the treatment of a given patient.

Figure 4:
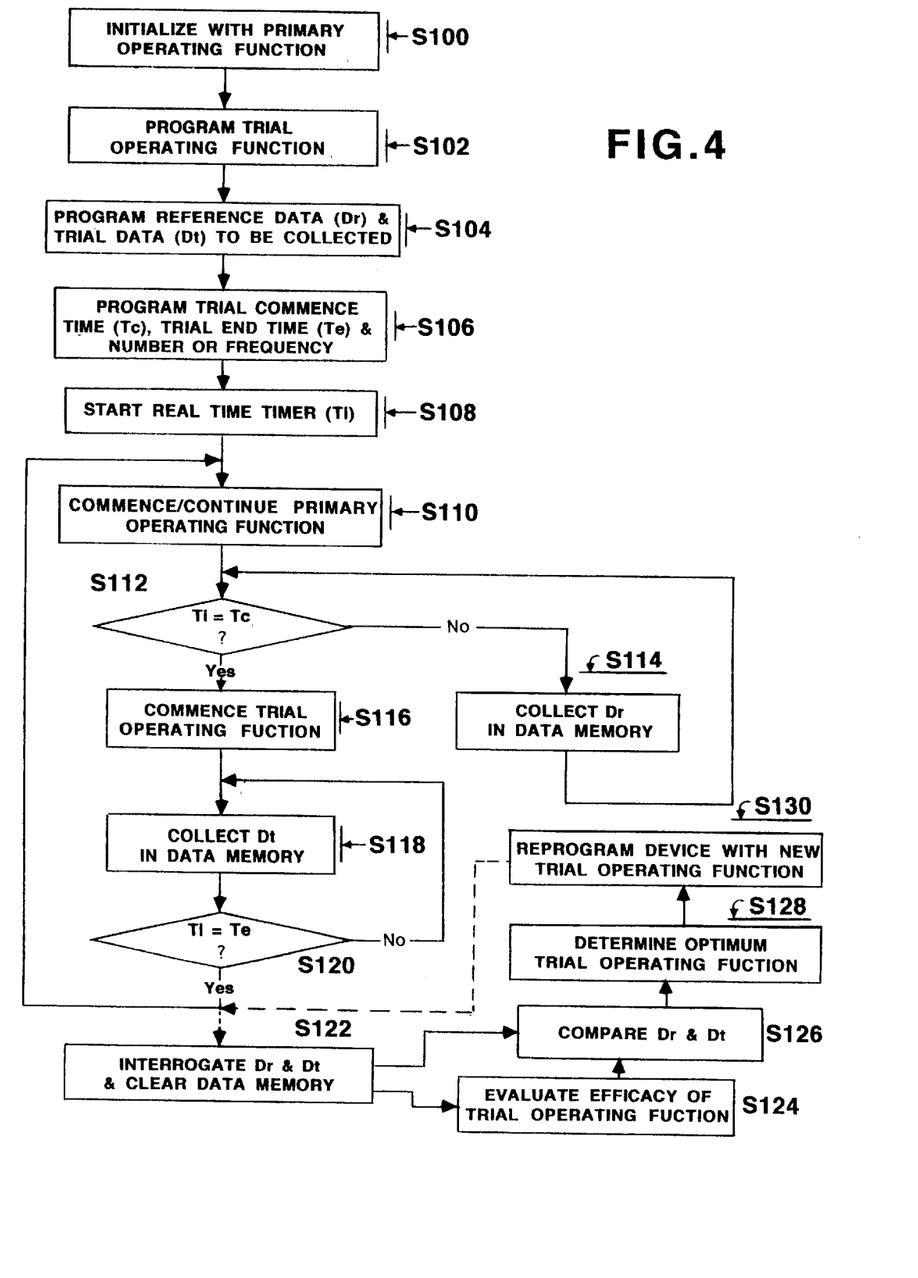
FIG. 4 shows a simplified flow chart illustrating the operation of the pacing system of the present invention, where the system acquires and stores reference and trial data.

The flow chart of FIG. 4 shows one method of the present invention. An implantable medical device such as a pacemaker has programmable memory unit 30 therein for storing one or more of a plurality of programmable sequences of operating instructions. Those instructions control patient condition monitoring or therapy delivery operations. For example, the operating instructions may constitute a primary operating function of a device or a control program in devices such as those disclosed in the above-referenced '691 and '692 patents. After the medical device is implanted in the patient, an external programmer is used to download, enable or modify the primary operating function in step S100. Contemporaneously, or at a later date, the physician programs the trial operating function in the device. In step S102, the operating function may constitute an operating mode or a parameter value corresponding to a method of therapy delivery or to a method of monitoring.

Next, the physician executes the remaining steps for testing the trial operating function and gathering trial data related thereto. The physician preferably also gathers control or reference data for comparison to the trial data.

Simultaneously, the physician programs in the reference data $D_r$ and the trial data $D_t$ to be acquired, the commence time(s) $T_c$ and end time(s) $T_e$ defining the trial time periods during which the trial operating function is enabled in steps S104 and S106. A specified number or frequency of trial time periods may be programmable or the trial time periods may be allowed to continue indefinitely at specified time(s) of each day or specified days or the like. Moreover, one or more algorithms stored in ROM/RAM unit 30 may be enabled through a respective programmable command to define the commence time(s) $T_c$ and end time(s) $T_e$ in fixed intervals as suggested above or in a random fashion if this option is selected, the trial time periods during which the trial operating function is enabled in steps S104 and S106 will be randomly defined, e.g. during various day and night time periods of varying duration and separation, to obtain sets of trial data and reference data during periods ensuring that the patient is engaged in a variety of activities or states of sleep and wakefulness. In each case, the stored data trial and reference data sets are accompanied by time and duration markers.

The current real time timer 25 is enabled in step S108 (or may already be enabled and operating in step S100). The patient is then allowed to assume normal activities at home or remains hospitalized for observation. In step S110, in the implanted device or IPG 10, the primary mode function is commenced or continued, including tracking the current time in real time timer 25. The controller/timer CPU 32 continuously compares the current time to the commence time $T_c$ and end time $T_e$ in steps S112 and S120, respectively. In the intervals following the end time $T_e$ and before a commence time $T_c$, the primary operating function prevails, and the reference data $D_r$ is acquired in step S114, processed in controller/timer CPU 32 and stored in certain readable data memory registers in RAM/ROM unit 30.

The trial operating function is commenced in step S116 and the trial data $D_t$ is acquired in step S118 in the trial period(s) between each successive commence time $T_c$ and end time $T_e$ and stored in certain other readable data memory registers in RAM/ROM unit 30. The storage of raw trial data $D_t$ and reference data $D_r$ may be on a FIFO basis in separate RAM registers or the data may be processed to develop summaries of the raw data to provide for efficient storage in various ways known in the art.

Steps S110–S120 repeat for the number of trial time periods specified in step S106 or continuously until the uses the external programmer to interrogate the memory registers in RAM/ROM unit 30 and retrieve the reference data $D_r$ and the trial data $D_t$ for use in evaluating the efficacy of the trial operating function in step S122. To accomplish this, the telemetry transceiver 34 responds to a preprogrammed or programmed interrogation command and telemeters the acquired and stored data out to an external programmer. In response to analysis of the monitored patient data, the physician may non-invasively program a further programmable sequence of operating instructions controlling a monitoring or a therapy operation of the pacemaker IPG 10.

The process of FIG. 4 may be repeated several times using alternative primary operating functions and trial operating functions and comparing the sets of trial and reference data to determine an optimum trial operating function. The external programmer may then be used to re-program the primary operating function with the optimum trial operating function.

As noted above, it is contemplated that the trial operating function may be prescribed on a trial basis, evaluated following the above method, and then prescribed on a permanent basis, if the evaluation establishes that it is beneficial to the patient. In this context, it is contemplated that a charge may be made for is the trial or permanent prescription.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to a multi-programmable microcomputer based control circuit 21 in the implanted medical device; the present invention may also be usefully practiced in similar configurations by means of a full custom integrated circuit. As a further example, such a circuit may take the form of a state machine in which a state counter serves to control an arithmetic logic unit to perform calculations according to a prescribed sequence of counter controlled steps. Additionally, the present invention may also find application in implantable medical devices other than those having cardiac applications such as in, for example, implantable medical devices for stimulating any tissue or organ, neurological stimulators, and gastrointestinal system stimulators.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

The present invention further includes within its scope methods of implanting, making and using implantable medical devices and components therefor as described hereinabove.

I claim:

1. A method of operating an implantable medical device, the device having an operating memory therein for storing a programmable sequence of operating instructions for controlling a primary operating function of the device, a data memory for storing acquired reference and trial data, and a telemetry system for telemetering stored data to an external programmer upon receiving a programmable interrogation command, the method comprising the steps of:

(a) enabling a sequence of operating instructions controlling a primary operating function of the medical device during a reference time period;

(b) acquiring reference data related to the primary operating function of the medical device during the reference time period;

(c) enabling a sequence of operating instructions controlling a trial operating function of the medical device in conjunction with implanting the medical device during a trial time period;

(d) acquiring trial data related to the trial operating function of the medical device during the trial time period, and (e) interrogating, using the external programmer, the memory of the device.

2. The method of claim 1, further comprising the step of retrieving, using the external programmer, from the memory reference data and trial data.

3. The method claim 2, further comprising the step of evaluating the efficacy of the trial operating function.

4. The method of claim 3, further comprising the step of repeating the preceding steps to determine an optimum trial operating function.

5. The method of claim 4, further comprising the step of re-programming, using the external programmer, the primary operating function in the device with an optimum trial operating function.

6. A method of providing a therapy or monitoring function in an implantable, programmable medical device, the therapy or function being under the control of a programmable sequence of operating instructions controlling an operating function of the implantable medical device, the implantable device having a telemetry transceiver for receiving external programmable sequences of operating instructions and for transmitting data externally from the implantable medical device, the implantable device having a memory for storing the sequence of operating instructions and for storing data related to the delivery of the therapy or the monitoring function, the implantable device being employed in conjunction with an external programmer for programming a trial operating function for a trial time period, the method comprising the steps of:

(a) programming the device to have a primary operating function or primary operating mode;

(b) programming the device to have a trial operating function or trial operating mode for delivery of the therapy or enablement of the monitoring function;

(c) programming the device to acquire reference data and trial data;

(d) programming the device with a trial time period during which the trial operating function is enabled;

(e) during each trial time period, operating the medical device in accordance with the trial operating function to acquire and store trial data in memory; and (f) at times other than during trial time periods, operating the medical device in accordance with the primary operating function to acquire and store reference data in memory;

(g) interrogating the memory of the implantable device; and (h) retrieving reference data and trial data stored in memory.

7. The method of claim 6, further comprising the step of evaluating the efficacy of the trial operating function.

8. The method of claim 7, further comprising the step of acquiring and storing successive sets of reference and trial data by repeating the steps of claims 7 and 8.

9. The method of claim 8, further comprising the step of comparing the sets of trial and reference data.

10. The method of claim 9, further comprising the step of determining an optimum trial operating function based on the comparison of the sets of trial and reference data.

11. The method of claim 10, further comprising the step of re-programming the device to have a new primary operating function that is based on the optimum trial operating function.

12. A method of providing a therapy or monitoring function in an implantable, programmable medical device, the therapy or monitoring function being under the control of a programmable sequence of operating instructions controlling an operating function of the implantable medical device, the device having a telemetry transceiver for receiving external programmable sequences of operating instructions and for transmitting data externally from the implantable medical device, the device having a current real time associated therewith and stored therein, the device having a memory for storing the sequence of operating instructions and data related to the delivery of the therapy or the monitoring function, the device being employed in conjunction with an external programmer for programming a trial operating function for a trial time period in the device, the method comprising the steps of:

(a) programming the device to have a primary operating function or primary operating mode;

(b) programming the device to have a trial operating function or trial operating mode for delivery of the therapy or enablement of the monitoring function;

(c) programming the device to acquire reference data and trial data;

(d) programming the device with a trial time period defined by a trial commence time and trial end time during which the trial operating function is enabled;

(e) timing out the current real time;

(f) comparing the current real time to the trial commence time, the trial end time and times therebetween to determine whether the current real time coincides with any portion of the trial time period;

(g) between the trial commence time and trial end time operating the medical device in accordance with the trial operating function to acquire and store in memory trial data;

(h) at times other than those defined by the trial commence time and trial end time, operating the medical device in accordance with the primary operating function to acquire and store in memory reference data;

(g) interrogating the memory of the implantable device; and (h) retrieving reference data and trial data stored in memory.

13. The method of claim 12, further comprising the step of non-invasively programming an additional programmable sequence of operating instructions in the memory for controlling operation of the device.

14. The method of claim 13, further comprising the step of repeating the steps of claims 12 and 13 in response to each termination of a sequence of operating instructions.

15. An apparatus for operating a medical device implanted in a patient, the device having an operating memory therein for storing a programmable sequence of operating instructions for controlling a primary operating function of the implantable medical device, the apparatus comprising:

(a) means for timing a trial time period and a reference time period;

(b) means for executing a sequence of operating instructions for controlling a primary operating function of the medical device during the reference time period;

(c) means for acquiring reference data related to the primary operating function of the medical device during the reference time period;

(d) means for executing a sequence of operating instructions for controlling a trial operating function of the medical device during the trial time period; and (e) means for acquiring trial data related to the trial operating function of the medical device during the trial time period.

16. The apparatus of claim 15, wherein the implanted medical device further comprises a data memory for storing acquired reference and trial data.

17. The apparatus of claim 16, further comprising a system for transmitting stored data out to an external programmer on receipt of a programmable interrogation command.

* * * * *